United States Patent [19]
Coetzee

[11] Patent Number: 5,924,980
[45] Date of Patent: Jul. 20, 1999

[54] METHOD AND APPARATUS FOR ADAPTIVELY REDUCING THE LEVEL OF NOISE IN AN ACQUIRED SIGNAL

[75] Inventor: Frans Martin Coetzee, Princeton, N.J.

[73] Assignee: Siemens Corporate Research, Inc., Princeton, N.J.

[21] Appl. No.: 09/038,334

[22] Filed: Mar. 11, 1998

[51] Int. Cl.[6] .................................................. A61B 5/00
[52] U.S. Cl. .................................... 600/300; 128/901
[58] Field of Search ........................... 128/901, 924–925; 600/300, 415, 475, 508, 509

[56] References Cited

U.S. PATENT DOCUMENTS

| | | | |
|---|---|---|---|
| 4,537,200 | 8/1985 | Widrow | 600/509 |
| 4,793,361 | 12/1988 | Dufault | 600/509 |
| 5,584,295 | 12/1996 | Muller | 600/300 |
| 5,704,365 | 1/1998 | Albrecht et al. | 128/901 |

Primary Examiner—William E. Kamm

[57] ABSTRACT

An adaptive filtering method and apparatus for reducing the level of an undesired noise component in an acquired physiological signal having a desired signal component. The acquired physiological signal is applied to one input of the adaptive filter, and a synthetic reference signal that is modeled so as to exhibit a correlation with the desired signal component is applied to another input of the adaptive filter. Thereafter, in a feedback manner, the adaptive filter iteratively adjusts the modeled synthetic reference signal so as to progressively generate a more accurate approximation of the desired signal component in the adaptive filter, which approximation becomes a reconstruction of the acquired physiological signal wherein the level of the undesired noise component is reduced.

25 Claims, 4 Drawing Sheets

METHOD AND APPARATUS FOR ADAPTIVELY REDUCING THE LEVEL OF NOISE IN AN ACQUIRED SIGNAL

BACKGROUND OF THE INVENTION

1. Field of the Invention

The present invention relates to a method and apparatus for adaptive filtering of a signal having a desired component and an undesired component, and more specifically, to reducing the level of an undesired noise component in a physiological signal by adaptive filtering of the physiological signal using a synthetic reference signal which is modeled to exhibit a correlation with the desired signal.

2. Description of the Prior Art

The measurement of various types of physiological signals is generally a difficult task because the underlying physiological processes that generate physiological signals generate such signals at very low amplitude levels. Additionally, during acquisition of the physiological signals, the physiological processes, and/or sensors associated therewith, typically also generate or become the sources for a noise component that becomes an undesired part of the desired physiological signals.

For example, when electrocardiogram (ECG) signals of a patient are measured, sensors detect not only the electrical activity generated by the electrical depolarization of the heart, a relatively weak signal by the time it reaches the skin of the patient, but also electrical signals, artifacts, generated by the activity of other muscles in the patient. Furthermore, external electrical interference, such as the 60 Hz line frequency signals and electrical signals emanating from nearby electrical equipment are also acquired as noise components of the desired physiological signal. Hereinafter, such noise and/or artifact signals are also referred to as the noise, artifact, or undesired component of the physiological signal.

Another common physiological signal measurement suffering from low levels of desired signal and relatively higher levels of the undesired component is the measurement of the blood oxygen saturation level of a patient using a pulse oximeter. As well known by those of ordinary skill in the art, a pulse oximeter measures arterial blood oxygen saturation using a sensor arrangement containing two LED's and a photodiode detector. The sensor is applied directly to a well perfused part of a patient, such as at a finger or ear. Each LED of the sensor transmits radiation at a different one of two wavelengths, typically one being red and the other being infrared, to the patient. The photodiode detector is responsive to the red and infrared light for developing red and infrared electrical signals that are affected, via transmission or reflection, by the patient's blood flow in the area between the two LED's and the light receiving portion of the photodiode detector. The greater the oxygenation of the blood, the less of the emitted red light is detected, due to greater absorption of the red light by the patient's blood. In pulse oximeters, the acquired red and infrared signals are processed to develop a measurement indicative of the current blood oxygenation level of the patient. Additionally the acquired light signals can be processed further to develop a measurement of the pulse rate of the patient, since, as well known, the pulsatile component of the light signals results mainly from ventricular contractions of the heart.

Processing of the red and infrared signals for determining blood oxygenation is based on the Beer-Lambert law, as well known, wherein a ratio is generally used to compare the AC and DC components of the red light ($AC_r$ and $DC_r$, respectively), to the AC and DC components of the infrared light ($AC_{ir}$ and $DC_{ir}$, respectively), in accordance with the following equation:

$$\frac{AC_r/DC_r}{AC_{ir}/DC_{ir}}$$

The resultant value is applied to an experimentally-determined reference table (look-up-table) to provide the final determination of the measured level of the blood oxygenation. Additionally, as noted above, the AC components of the signals can be further processed to generate an estimate of the pulse rate.

The blood oxygenation and pulse rate measurements made from optically acquired signals are highly prone to inaccuracies due to the undesired noise and/or artifact components of the acquired signal. The noise components typically result from electrical interference (lights, electro-surgical and other electrical equipment being operated near the patient), and artifacts typically result from patient movement (causing a relative movement, and concomitant change in light path, between the LED's and detector of the sensor, or even worse, the sudden admission of room light into the receiving area of the photodiode detector). Furthermore, the AC component of the acquired signals (which result from the pulsatile characteristic of the blood), is very small, typically on the order of only 1%–5% of the DC value of the acquired signals, as is also typical of physiological signals. Consequently, such noise and artifacts are extremely detrimental to accurate pulse oximetry measurements, leading to the serious problem of an incorrect assessment of the patient's condition, as well as false alarms to the user of the oximeter.

U.S. Pat. No. 4,955,379 entitled MOTION ARTIFACT REJECTION SYSTEM FOR PULSE OXIMETERS, issued Sep. 11, 1990, discloses a band-pass filtering (BPF) technique for removing noise artifacts from pulse oximetry signals. More specifically, the AC components of each of the acquired red and infrared signals is initially filtered by a BPF that is broadly tuned to the expected heart rate frequency. The output of the BPF is applied to a frequency determining circuit, whose output is then used to cause the BPF to track the frequency determined by the frequency determining circuit. The theory of this technique is that most of the energy (and information) in the AC signal is contained at the fundamental frequency, and since the fundamental frequency should be the pulse rate, the frequency determining circuit will determine the pulse rate as the fundamental frequency and control the BPF to exclude all other frequencies, along with artifacts. Unfortunately, it is quite possible that the fundamental frequency determined by the frequency determining circuit may in fact be a noise signal, such as one that is generated by electrical equipment, causing the oximeter to process the signal and report erroneous information. Furthermore, even if the fundamental frequency of the pulse rate is correctly determined, since other frequency components of the desired pulse signal are excluded, a degraded performance of the oximeter can result. Consequently, this technique is undesirable.

U.S. Pat. No. 4,928,692 entitled METHOD AND APPARATUS FOR DETECTING OPTICAL PULSES, issued May, 29, 1990, discloses a technique wherein the R-wave portion of a patient's ECG waveform is correlated in time with the optical signals acquired by a pulse oximeter. The correlation is used to develop an enabling signal for processing of the acquired optical signals by the oximeter. The theory is that since the pulsatile component of the optical signals contain the information, and the occurrence of the pulses can be predicted to follow an ECG R-wave by a certain amount, selective timing of oximeter enablement will prevent artifact from being admitted into the oximeter and erroneously processed. Unfortunately, since artifacts can occur at any time, and in general are not in any way correlated so as to have any relation to occurrence of an ECG R-wave, this technique is also undesirable.

U.S. Pat. No. 5,482,036 entitled SIGNAL PROCESSING APPARATUS AND METHOD, issued Jan. 9, 1996 is representative of a technique that uses an adaptive noise cancellation filter for reducing noise in pulse oximetry signals acquired using a sensor arrangement having two light sources. FIG. 5 of this prior U.S. Pat. No. 5,482,036, illustrates the application of linear adaptive noise cancellation to pulse oximetry. The acquired signal $S_{\lambda a}$ comprises two components: a desired signal component $Y_{\lambda a}$ (a modulation signal that would be obtained from a pulse oximeter under ideal conditions), that is additively combined with a noise signal component $n_{\lambda a}$. A reference signal n' that has a significant similarity to the noise component is provided. The objective of the cancellation filter is to transform the reference signal n' into a signal $b_{\lambda a}$ having as close an approximation of the noise component $n_{\lambda a}$ as possible. Then, by subtracting the noise component approximation from the contaminated signal, a reconstruction $Y'_{\lambda a}$ of the uncontaminated component of the input signal is obtained. Conversely, a reference signal n' that has a significant similarity to the desired signal $Y'_{\lambda a}$ can be provided, and an approximation $Y'_{\lambda a}$ built up for $Y_{\lambda a}$ using operations on n'. Built up signal $Y'_{\lambda a}$ can then be used as the output of the cancellation filter. The basic idea is that if the reference signal contains substantial information about only one, not both, of the two input signals, the input signal $S_{\lambda a}$ can be separated into some approximation of the desired signal component $Y_{\lambda a}$ and some approximation of the noise signal component $n_{\lambda a}$.

However, in pulse-oximetry, a reference signal is not readily available. In the forenoted U.S. Pat. No. 5,482,036 a reference signal is generated from the measured lead signals using a technique based on the fact that the desired portions of the acquired red and infrared signals are linearly related at a given level of blood oxygen saturation. More specifically, the acquired red and infrared signals are subtracted from each other after determination of an appropriate scaling factor w, for generating the approximation of the noise component, which approximation is then used as the reference input to the adaptive filter to develop a reconstruction of the desired signal. However, a significant problem with the above technique is that by combining the acquired signals to generate a reference signal that describes the noise component, some part of the desired component s may be included in the reference signal. Consequently, the desired signal s, or a portion thereof, will be erroneously identified as noise, thereby causing significant errors in reconstruction of the desired signal. The same problem exists if the system is operated conversely, where the acquired red and infrared signals are subtracted from each other after determination of a different appropriate scaling factor w, for generating a signal substantially similar to the desired signal component s, which approximation is then used as the reference input to the adaptive filter. In the latter case some part of the noise component n may be included in the reference signal, thereby also causing significant errors in reconstruction of the desired signal.

It would be desirable to provide a more reliable manner of reducing the noise component in an acquired physiological signal.

As will be described next, the present inventor has discovered that in an adaptive cancellation arrangement, to reduce noise and other artifacts from a desired component of a noisy signal, when the basic structure of the desired signal is known, knowledge of the basic structure can be used to improve the operation of the adaptive cancellation arrangement.

SUMMARY OF THE INVENTION

In accordance with the principles of the present invention, an acquired physiological signal which may be contaminated with noise, comprising a desired signal component and an undesired noise component, is applied to one input of an adaptive filter, and a synthetic reference signal that is modeled so as to exhibit a correlation with the desired signal component is applied to another input of the adaptive filter. Thereafter, in a feedback manner, the adaptive filter iteratively adjusts the synthetic reference signal so as to progressively generate as an output of the filter a more accurate approximation of the desired signal component, which approximation becomes a reconstruction of the acquired physiological signal wherein the level of the undesired noise components are reduced. As a result of the invention a more accurate and reliable reconstruction of the physiological signal is developed.

In accordance with a further aspect of the invention, asynchronously with the operation of the adaptive filter arrangement, the acquired physiological signal is processed so as to identify signal sections thereof having a high confidence of being free of undesired noise components, i.e., representative of only the desired signal component. These high confidence sections are then analyzed to generate additional knowledge about the desired signal component, which knowledge is periodically used to adjust the synthetic reference signal so that a more accurate representation of the desired signal component of the acquired physiological signal is applied as a reference signal to the adaptive filter arrangement.

In one embodiment of the invention having first and second pulse oximetry signals as the acquired signals, the pulse oximetry signals are compared with each other, as well as past segments of themselves and each other, so as to generate the high confidence signal sections. These sections are then processed so as to develop phase and frequency information about the desired signal component, which is used to modify the phase and frequency components of the synthetic reference signal. In addition, the high confidence signal sections themselves can be used to directly modify the shape of the modeled synthetic reference signal.

In an alternative embodiment of the invention a different type of physiological signal, such as an EKG signal, may be processed so as to develop one or more types of adjustment inputs for the modeled synthetic reference signal.

DETAILED DESCRIPTION

Figure 1:
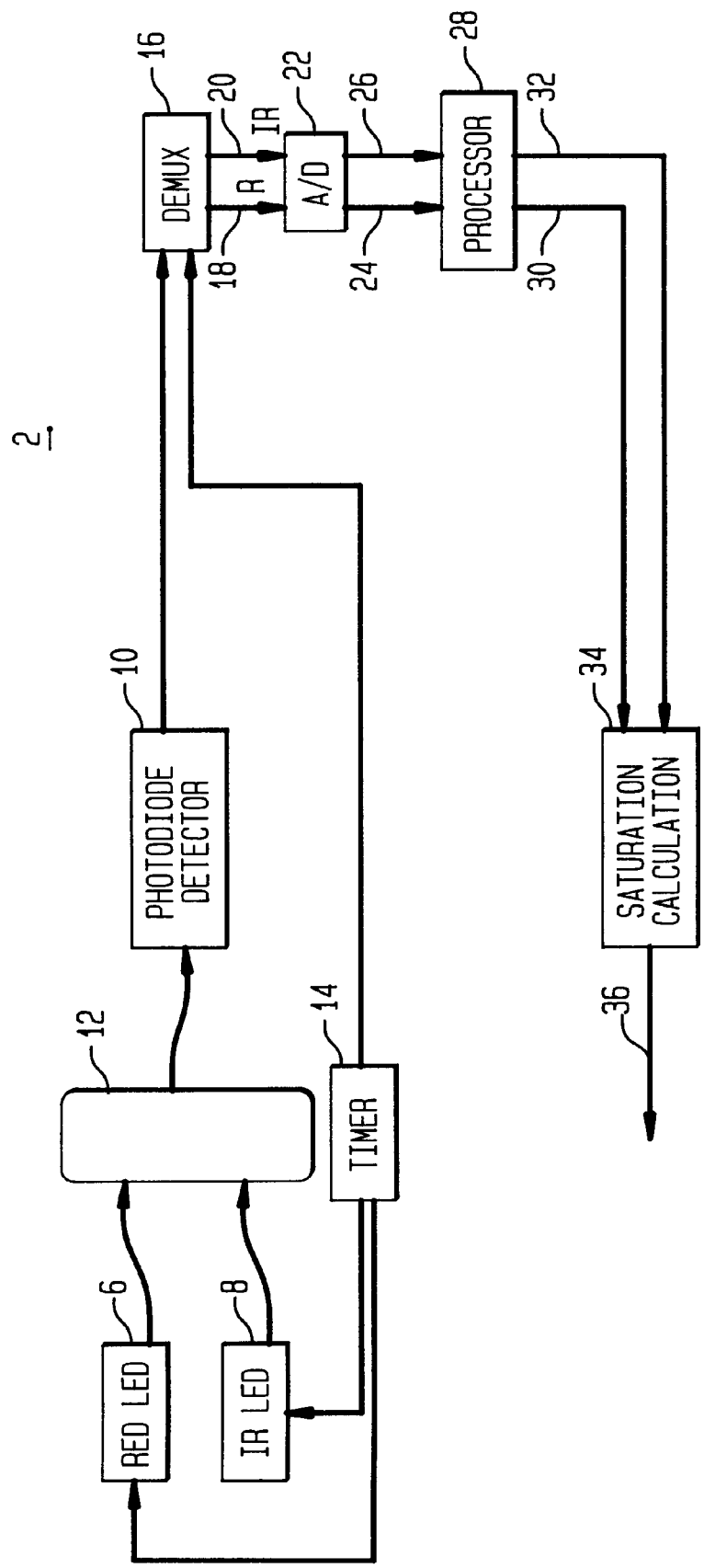
FIG. 1 illustrates in block diagram form the operation of a pulse oximeter in accordance with the principles of the invention.

In the following detailed description, an exemplary embodiment comprising a pulse oximeter is described, however, it is noted that the techniques of the present invention are broadly applicable to reducing the noise and artifact components in other types of physiological signals, such as EKG signals, as well as other types acquired signals. Referring to FIG. 1, a physiological monitor 2 is shown having a sensor arrangement 4 comprising, as well known, red 6 and infrared 8 LED's and a photodiode detector 10 arranged in an opposed spatial relationship in a housing, not specifically shown, which is attached to a well perfused part of the patient, such as a finger 12 or alternatively on an ear. A timer 14 causes LED's 6 and 8 to operate in a pulse manner (say at 400 Hz), as well known, so as to cause photodiode detector 10 to develop at its output red and infrared oximetry electrical signals in a time division multiplexed manner. A demultiplexer 16 of conventional design, is responsive to timer 14 and the time division multiplexed signals, for developing analog red and infrared oximetry electric signals 18 and 20, respectively. An analog to digital converter 22 develops digitized (say at 100 Hz) red and infrared oximetry electrical signals 24 and 26. As previously described, the acquired oximetry signals are prone to relatively severe noise contamination, thereby hindering their use as reliable indicators of blood oxygenation. Consequently, the digitized oximetry signals 24 and 26 are provided to a processor 28 for noise reduction processing in accordance with the principles of the present invention, for developing at the output of processor 28 noise reduced digital red and infrared oximetry signals 30 and 32. In accordance with conventional knowledge, the nominal ratio of successive samples of the red and infrared signals is calculated in a saturation processor 34 and converted to a saturation estimate. Saturation processor 34 provides at its output a series of estimated values 36 for the blood oxygen saturation of the patient, which are then used as the current blood oxygen saturation estimate output of monitor 2, by use of a display, recorder or transmitter, not specifically shown.

As previously noted, the acquired physiological signals include a desired pulsatile component that is easily contaminated with noise signals, i.e., artifact, which disturbs the above-noted ratio processing, resulting in an inaccurate saturation estimate, and even the generation of false alarms by monitor 2. The exact effect of the artifact upon the saturation estimate depends on the specific processing used to develop the estimate.

One way to eliminate the saturation estimate error is by an attempt to completely separate the desired pulsatile signal from the artifact. A central difficulty with applying the forenoted existing noise cancellation approaches to solve this problem, results from the fact that there is no clean reference signal available to use in an adaptive filter, and that the artifact cannot be adequately characterized in a statistical sense. The present inventor has realized that the only reasonably knowable information about the reference signal, lies in the fact that the desired pulsatile signal derives from a process which can be reasonably characterized.

Thus, in accordance with the present invention, processor 28 generates a synthetic reference signal that exhibits a correlation with the desired pulsatile signal, and uses the synthetic reference signal to train an adaptive filter to track the desired pulsatile signal component in the acquired contaminated oximetry signals 24 and 26.

In accordance with a first aspect of the invention, two major parameters are used to calculate the synthetic reference signal, i.e., the synthetic pulsatile heart rate signal, given a canonical wave-shape. These parameters are the phase and the frequency of the desired heart rate signal.

In accordance with a second aspect of the invention, estimation of the phase and frequency of the desired heart rate signal is performed by suitable processing of the contaminated oximetry signals. In an alternative embodiment of the invention, estimation of the phase and the frequency of the desired heart rate signal can be performed by suitable processing of an additionally acquired further physiological signal, such as an ECG signal. Such suitable processing for an ECG signal is well know by those of ordinary skill in this technology.

Processing in accordance with the invention can be divided into two parts: section I, estimation, and section II, filtering. The estimation section extracts heart rate information from relatively low-noise regions of digitized lead signals 24 and 26 to help generate a more accurate synthetic reference signal. This section processes asynchronously to the filtering section. The filtering section uses the synthetic reference signal to continuously filter noise contaminated signals 24 and 26 to calculate the saturation estimate values.

The major stages of section I of the signal processing are as follows:

1. Signal conditioning
   a. Baseband filtering
   b. Baseline removal
2. Outlier detection and confidence tagging
   a. Amplitude outlier detection
   b. Interlead correlation detection
   c. Morphological error sequence processing
3. Heart rate estimation, and
4. Synthetic Signal Generation The major stages of section II of the signal processing are as follows:

5. Adaptive filtering
6. Subspace projection and saturation calculation
7. Saturation estimate filtering Signal Conditioning Reference is now made to FIG. 2 which illustrates the above signal processing steps. Initial signal conditioning comprises a logarithmic transformation stage 202, a baseband filtering stage 204, and a linear spline baseline removal stage 206.

At stage 202, the logarithm of each sample s[n] of digital signals 24 and 26 is taken, for introducing linearity properties to the intensity-based (i.e., exponential) signals 24 and 26, thereby developing corresponding lead signals 208 and 210, respectively. Signals 208 and 210 are then filtered using a Butterworth low pass filter 204 having an upper cutoff frequency of 5 Hz, corresponding to 300 bpm, for producing signals 212 and 214 which are applied to stage 206 for removal of the baseline portion of signals 212 and 214, as next described.

Proper operation of the pulse oximeter depends on the ability to normalize the acquired signals with respect to the DC light level. In current systems, the present inventor observed that even under what would be considered clinically optimal conditions, there is a significant amount of baseline wander. Therefore, it is not obvious how to normalize the received signal.

Under ideal circumstances, the normalization of the base signal (up to a small DC offset), is equivalent to high-pass filtering of the signal with a very high-order filter. This interpretation suggests that the baseline wander can be removed by high-pass filtering. However, oximeters should be capable of processing heart rates over a very large range, such as from 15 bpm (beats per minute) to 300 bpm. Careful spectral analysis of acquired oximetry signals show that the spectrum of the baseline wander signal overlaps the spectrum of the pulsatile waveform. Since insufficient statistical information about the relevant spectra are available, standard techniques (e.g. Wiener filtering), cannot be used to design a linear filter that, in general, can remove the baseline wander.

In accordance with a further aspect of the present invention, in a preferred embodiment of the invention, baseline removal is accomplished using a delay buffer of length M (say 500 samples) to buffer data samples s[n] of each of signals 212 and 214. Each incoming signal sample is evaluated to check whether it is a unique maximum in a window of length L (say 30 samples). If it is the unique maximum in such a region, it is tagged as being so, and a linear fit consisting of an estimate of the offset and of the slope is calculated, based on the value and time index of the previously obtained maximum value and the new time index and local maximum value. The linear fit is used to calculate a baseline estimate for all the samples with time indices between the two local maxima and then the baseline estimate is subtracted from the signal, thereby generating fully conditioned red and infrared digital signals 216 and 218, respectively. If no new local maxima have been found and the buffer overflows, the current offset and slope estimate is used to filter the data until valid maxima are obtained.

While it would appear that this procedure is sensitive to spike noise, during tests the above baseline removal procedure performed significantly better than a baseline removal stage comprising a linear IIR filter.

Outlier Detection and Confidence Tagging

The next step in section I of the signal processing is outlier detection and confidence tagging. This is accomplished by stage 220 shown in FIG. 2. Stage 220 comprises outlier detection stages 222, a correlation detector stage 224 and a morphological filter stage 226, that results in the generation at the output of stage 220 of a stream of final error codes 228 that tag (identify) sections in lead signals 216 and 218 that have a high confidence level of being relatively noise-free. The major purpose of stage 220 is to learn gross statistics about each of lead signals 216 and 218, and to associate with each signal sample s[n] of these signals, an associated error code, $\tau$ [n], which indicates whether that signal sample is considered highly contaminated by noise. In stage 220, each of a plurality of statistical tests generates a specific error code, so that multiple error codes become associated with each signal sample. The resulting error codes are then taken into account in the subsequent processing stages, as will be described next.

As noted above, one of the statistical tests of stage 220 comprises interlead correlation detection. As previously noted, the red and infrared LED's are operated in a pulsed manner, causing the correspondingly acquired optical oximetry signals to be time-division multiplexed. Due to the close spatial proximity of the LED's and the relatively fast multiplexing (400 Hz switching), and a 100 Hz signal digitization for each signal lead, the absorption representative components of digital signals 216 and 218 change in a highly correlated way. Accordingly, in the preferred embodiment of the invention, the correlation detector stage 224 correlates sections of window length M (say 200 samples), centered around each sample s[n] of the digital signals 216 and 218. If the correlation coefficient between the two sections of signal samples is less than a vigilance parameter $\rho_{corr}$ (say 0.98), then those signal samples s[n] are tagged as invalid based on insufficient correlation, and a corresponding error code signal 230 is provided.

Particular motion artifacts, especially evident in neonates, are sudden large spikes and swings in the baseline amplitude level, which are orders of magnitude larger than the nominal signal value. Accordingly, the second statistical test of stage 220, performed by amplitude outlier detection stages 222, is used to detect these regions in signals 216 and 218. Amplitude outlier detection has to have the capability of being robust against spike outliers of almost arbitrary magnitude relative to the nominal size of the AC component.

A simple linear filter (such as a mean filter), would fail to detect these regions since the spikes contain large amounts of energy which would skew the mean towards the outlier regions. Furthermore, since A/D converter 22 is not connected in a feed-back loop, the size of the AC component of the acquired signals can not be determined with reasonable accuracy. Consequently, based on skin to probe pressure, skin pigmentation and perfusion level, the magnitude of the AC component of the acquired signals is subject to large changes. The purpose of amplitude outlier detection is therefore two-fold:

1. To establish an estimate of the absolute magnitude and swing of the AC signal component of the acquired signals, and
2. To establish a detection mechanism to determine with high probability when excessive signal swings are present.

In accordance with a further aspect of the invention, the mechanism that is used to adaptively characterize the expected signal swing magnitude, is to maintain a histogram of the swings of each of signals 216 and 218 over a large time window. From each such histogram a Cumulative Distribution Function (CDF) is calculated. From the CDF the median signal value is calculated, which is a robust statistic from which an estimate of the nominal signal value for each signal is generated, as well as an outlier detection amplitude threshold. In the preferred embodiment, the nominal signal amplitude has a ratio G relative to the median, and a detection threshold is set at a value larger than this nominal signal value for each of signals 216 and 218.

Each histogram is calculated by maintaining a buffer of signal samples over a large time period up to the present (say 3000 samples), and updating the histogram periodically (say every 500 samples). On startup, the buffer can be initialized either by using a default expected signal swing (such as can be calculated by standard means from a database of clean reference data files that are decomposed into AC and DC components using a high pass filter having a lower corner frequency of 30 bpm), or by calculating an initial CDF using some small set (such as the first 500) samples obtained by outlier detectors 222 after the monitor is first switched on.

To calculate an estimate of the ratio G of the nominal signal amplitude expected relative to the median amplitude of the signal, the present inventor obtained artifact-free reference data from six patients, and the CDF of the magnitude of the reference signals was calculated. The 95 percentile value ($\eta 95$) and the median ($\eta 50$) value was found from the CDF for each of these patients. The 95 percentile value and the median value were then plotted against one anther, for the case when spline baseline signal removal in accordance with stage 206 was used. From these plots, the inventor realized that:

1. The ratio of the $\eta 50$ value to the $\eta 95$ value is approximately constant across the reference signal database, and
2. The ratio of the $\eta 95$ value to the $\eta 50$ value is approximately 2.228.

Using the ratio value of 2.228 as an estimate of G, an outlier detection amplitude threshold is then set conservatively at an amplitude value larger than (typically some multiple such as twice) the value of $\eta 50 \times 2.228$, measured in log(A/D) units. Setting the detection threshold in this manner ensures that an overwhelming fraction, typically more than 95%, of the data samples of a clean signal will be validated by amplitude outlier detection stages 222.

In the illustrated embodiment, a separate amplitude outlier detector stage 222 processes each of signal leads 216 and 218, and their outputs are combined on a logical OR manner to provide an error code signal 232 having a sequence of error codes that indicate an error condition whenever a corresponding portion of at least one of signals 216 or 218 has an amplitude swing that exceeds the previously determined detection threshold.

At the input of morphological filter 226, error code streams 230 and 232 provided from correlation detector stage 224 and the outlier detector stages 222, respectively, are combined using a simple logical (OR) rule, thereby indicating whether the corresponding data samples s[n] in signals 216 or 218 exceed the upper limit set for the amplitude magnitude, and/or whether the interlead correlation vigilance has been exceeded.

In order to ensure that no small, isolated regions, of signal data are tagged to be invalid and, furthermore, that no small, isolated regions, are tagged as valid, since such small isolated regions are likely to be tagged inappropriately, the morphological filter stage 226 performs erosion and dilation processing of the OR-ed error code stream.

In a first portion of filter 226, the error code stream is eroded to ensure removal of contiguous code sequences where the data samples are tagged as valid but which sequences have a length less than some specified number M (such as 20) of data samples. This procedure reduces the chance that isolated samples of low-confidence data which occurs in high-noise regions are inappropriately identified as being valid. In a second stage of filter 226, the thus eroded signal is then dilated, i.e., the error code is changed to indicate valid in contiguous blocks of error codes which indicate corresponding data samples that are tagged to be invalid but where the code sequence length is less than L (say 10) data samples. This ensures that small sections of signal sample data tagged to be invalid but which occur in regions where most of the signal samples are tagged to be valid, are not inappropriately removed. Finally, the thus modified error code stream is eroded by removing K (such as 3) samples from each end of every error code sample sequence which indicates corresponding data samples that are tagged to be valid, since such error codes occur where there is a change from a high-confidence region to a low-confidence region, and at these transitions data samples are more likely to be corrupted. As a consequence of the above morphological processing, the final error code stream 228 comprises contiguous blocks of some minimal size of the same error value, whereby the high-confidence regions of signals 216 and 218 can be clearly identified.

Heart Rate Estimation

Figure 2:
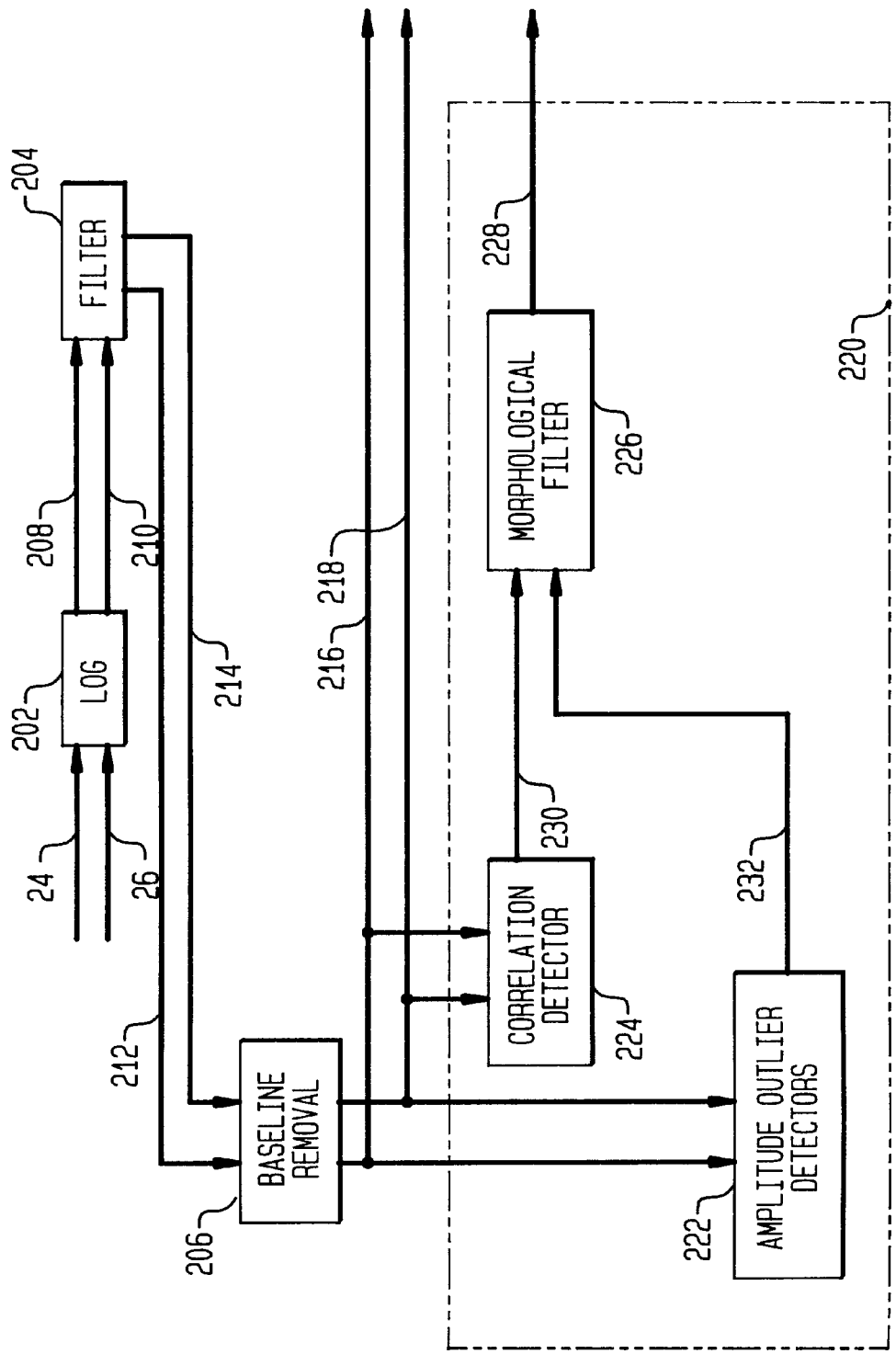
FIG. 2 illustrates in block diagram form a portion of the operation of the processor shown in FIG. 1.
Figure 3:
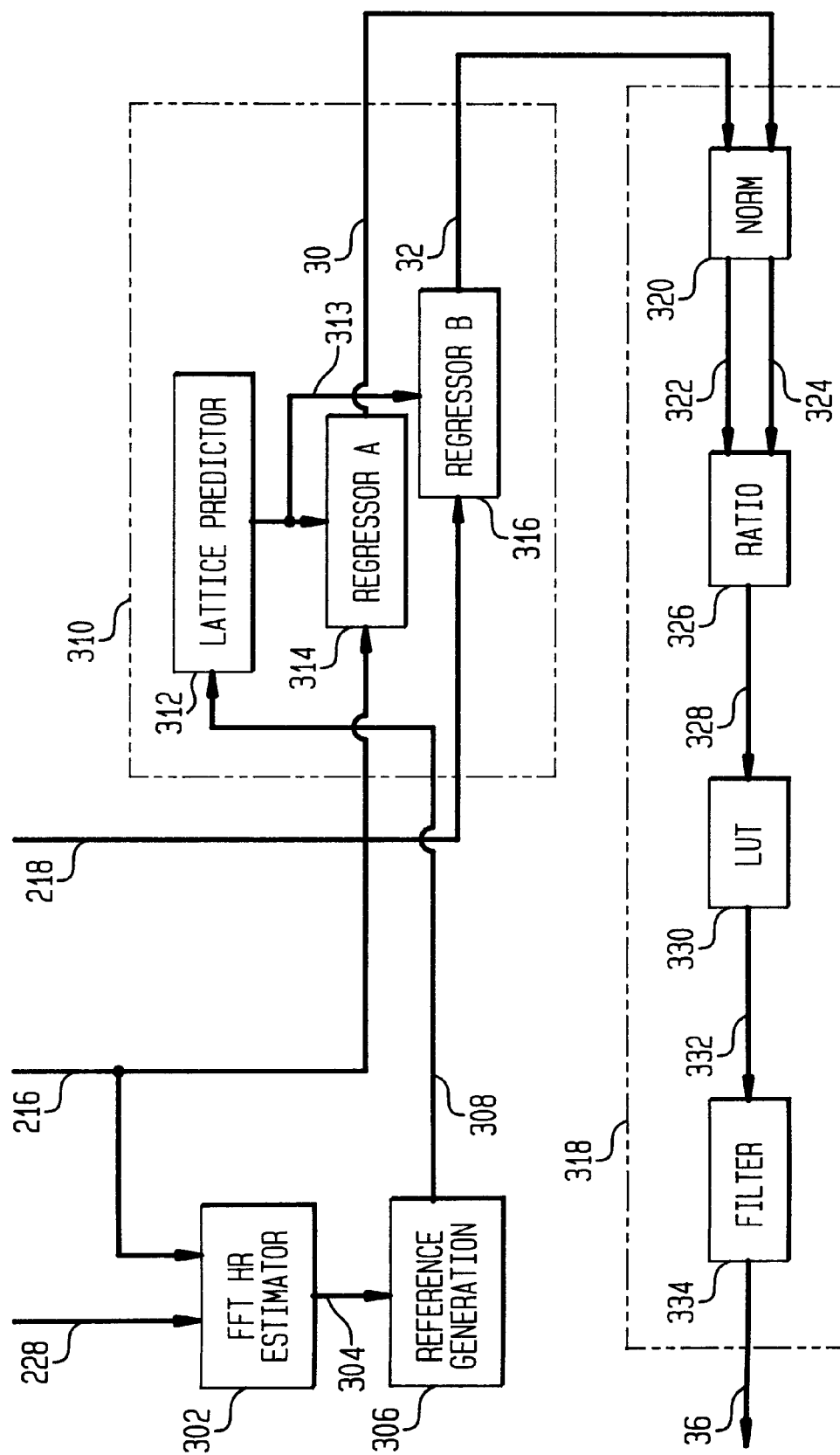
FIG. 3 illustrates in block diagram form the remainder portion of the operation of the processor shown in FIG. 1.

Any reliable estimate of the heart rate, such as can be obtained by processing of an ECG signal, if available, can be used. However, in the illustrated embodiment of an oximeter, an ECG signal is not available. Consequently, the above described processing of FIG. 2 is used to identify the high-confidence regions of signals 216 and 218, and an estimate of the patient's heart rate is then calculated directly from these regions. As shown in FIG. 3, an FFT estimator 302 is used for calculation of the heart rate estimate. FFT estimator 302 is responsive to the error code sequence 228 and one of the digitized lead signals, in the illustrated embodiment lead signal 216, so that the FFT processing takes into account only the high-confidence regions of signal 216. Accordingly, only the data samples which are tagged as valid are used in the FFT calculation, and the rest of the data samples are set equal to zero. A window of M data samples is used by FFT estimator 302, which samples are placed in a buffer having a length $L \geq M$, where the buffer is further filled in with zero values (i.e., zero-padded) when L>M. The number of samples M used, determines the step response of estimator 302, i.e. how fast the FFT can detect a change in heart rate of the patient. The step response for a distinct change in frequency which is detectable based on the resolution of the FFT, corresponds to a delay of M/2. The size of the FFT buffer L determines the resolution of the calculated heart rate estimate. For a sampling frequency $f_s$, the frequency resolution (in Hz) is given by:

$$\Delta f = f_s / L$$

After the FFT is calculated, the spectrum corresponding to signals below the lower and above the upper detectable heartrates, $hr_{min}$ and $hr_{max}$ respectively, are zeroed out. The power of the FFT is then calculated, and the primary peak index $k_{max}$ is determined. A heart rate estimate 304 is provided at an output of estimator 302, which is given by $$f_{hr} = k_{max}/L \bullet f_s$$

Furthermore, the fraction of the M data samples which are tagged as valid is kept track of in the system. If the fraction is above a preset threshold $\rho_{FFT}$, the new heart rate is accepted; if the fraction falls below the threshold, indicating very noisy data samples, the old heart rate estimate is maintained. The FFT output estimates 304 are updated every K seconds.

The following values were used in tests of the invention:

| Parameter | Symbol | Value |
| --- | --- | --- |
| FFT Length | L | 8192 |
| FFT Window | M | 1500 = 15 s |
| FFT Update Rate | K | 500 samples = 5 s |
| Sample Rate | $f_s$ | 100 Hz |
| Vigilance Parameter | ρ | 0.7 |
| Heart Rate Resolution | $\Delta f$ | 0.732 bpm |

Reference Signal Generation

Still referring to FIG. 3, a reference signal generator 306 generates a synthetic pulsatile reference signal 308, that models the arterial pulse component of the acquired lead signals, and from which an approximate basis for the subspace spanned by the arterial pulse component can be generated. The received signals 216 and 218 are projected by an adaptive filter 310 onto the subspace and noise is reduced by this operation. In accordance with the preferred embodiment of the invention, the basis is generated by a set of frequencies corresponding to the spectrum of the synthetic reference signal. The fact that a synthetic basis is used implies that an approximation error could exist between the basis spanned by the synthetic signal subspace and the basis spanned by the true pulsatile heart signal. The technique of the present invention depends only on the existence of a component of the true pulsatile absorption signal being in the subspace of the synthetic pulsatile reference signal, since the adaptive filter can build up appropriate kernels using simple operations on the reference signal. Since large artifact noise frequently appears at low frequencies, even after baseline removal, it is advisable to choose the synthetic reference signal to have a zero mean, thereby reducing spectral overlap.

Figure 4:
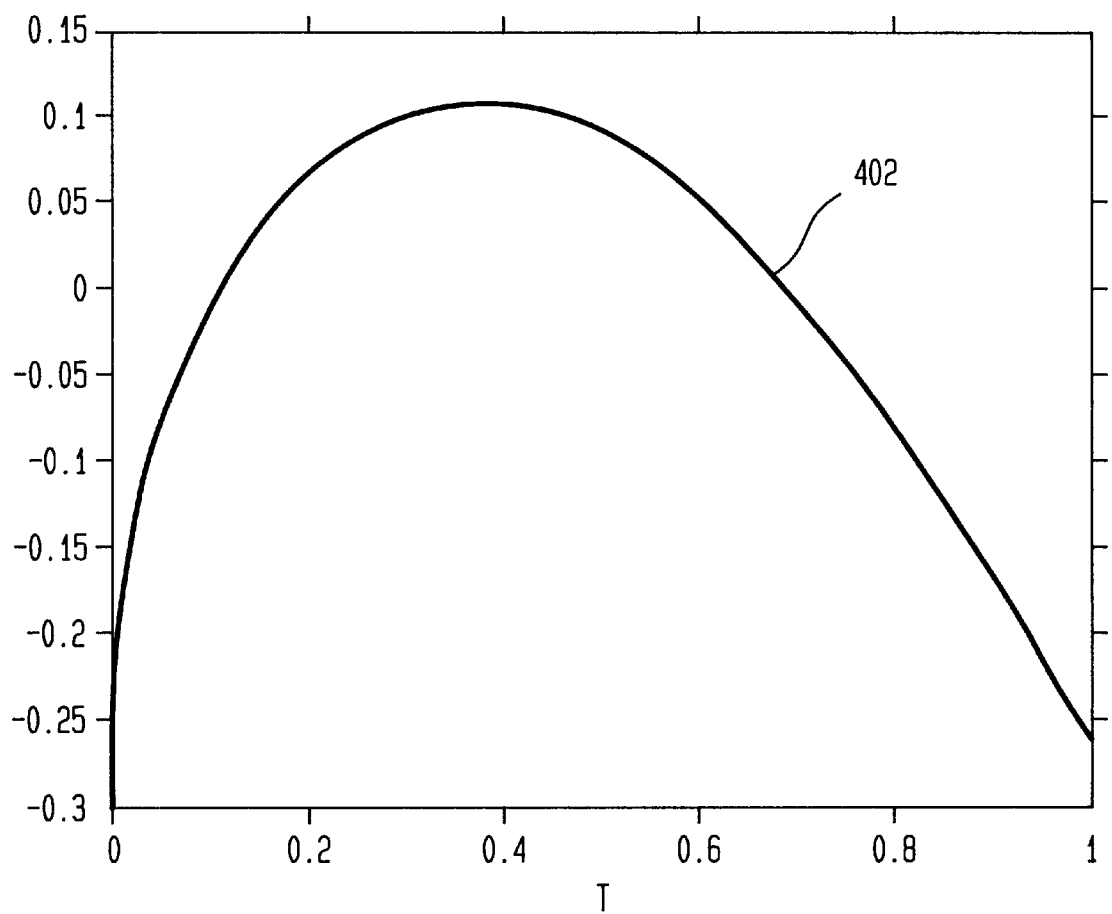
FIG. 4 illustrates the synthetic reference signal used in the processor shown in FIG. 1.

Referring to FIG. 4, the generation of the synthetic reference signal is performed by tracing out a kernel function 402 representative of the pulsatile component for a single cardiac cycle, at a rate equal to the heart rate. Kernel function 402 is the reasonably-knowable part of the desired pulsatile signal, and is generated so as to have a significant correlation to the desired pulsatile component of the acquired signals. The overall shape of the kernel derives from the physiological operation of the cardiopulmonary system, as has been well studied and is described in, for example, Chapter 2 (Heart Sounds and Murmurs) of the book "Physiology of Heart Disease" ed. L. S. Lilly. As described in this reference, the cardiac cycle produces a pressure waveform which is roughly triangular, with a fast increase in pressure as the left ventricle contracts, and a slower decay in pressure after the aortic valve closes. In the default implementation, a beta kernel was used which has a similar behavior of a fast rise time and slow decay, when defined by $$\psi(t;x,y)=t^x(l-t)^y-u_x$$

where x=0.5, y=1.0, and mu__x ensures zero mean and has a value of approximately 0.2663936. The frequency content of this kernel overlaps that of most expected patient cardiac cycle waveforms, and biases the kernel which is finally produced by the adaptive filter towards physically realizable waveforms.

In the preferred embodiment of the invention, reference signal 308 is generated using kernel 402, as defined by:

$$f(t)=\psi((\theta(t) \bmod 1)$$

where the instantaneous phase θ(t) is defined by $$\theta(t)=f_{hr}(t)(t-\phi(t))$$

where $f_{hr}$ (t) is the instantaneous heart rate and φ(t) is a phase term. The phase term is required to ensure continuity of the signal output when the heart rate frequency estimate changes discontinuously. In particular, if at time to, the heart rate changes from $f_{hr}^-$ to $f_{hr}^+$ the phase estimate φ⁺ is given by the convex combination $$\phi^+ = t_0\left(1 - \frac{f_{hr}^-}{f_{hr}^+}\right) + \phi^-\left(\frac{f_{hr}^-}{f_{hr}^+}\right)$$

In summary, the reference signal is generated by repeating the kernel function at a rate equal to the current estimate of the heart rate, and with an appropriate phase chosen to prevent discontinuities in the data at the point in time when the heart rate last changed.

Adaptive Filtering

Referring again to FIG. 3, an adaptive filter 310 is shown, responsive to signals 216 and 218 (the digitized versions of the noise contaminated acquired signals 18 and 20 of FIG. 1), and the synthetic reference signal 308. As is conventional in adaptive filter operation, internal to adaptive filter 310, synthetic reference signal 308 is gradually adjusted so that it becomes a more accurate approximation of the applied reference signal, i.e., the desired pulsatile component of each of signals 216 and 218. FIG. 3 conceptually illustrates a preferred implementation (due to its high numerical efficiency) of an appropriate adaptive filter 310, known as a joint process estimator. The theory and implementation of such a filter is well known, such as described in Chapter 15 of the book titled ADAPTIVE FILTER THEORY, by Simon Haykin published by Prentice Hall of Upper Saddle River, N.J.

Briefly, adaptive filter 310 can be separated into several main processing blocks. In a first processing stage 312, the applied reference signal, μ, is shifted and weighted by a multistage lattice prediction filter (Haykin FIG. 15.6), which generates a new set of orthogonal signals from μ, namely backward prediction errors 313 that span the same subspace as the reference signal and M of its versions, by adapting a set of coefficients using well known equations, as also described by Haykin.

For each signal to be filtered, namely the noise contaminated red and infrared lead signals 216 and 218, a respective regressor stage 314 and 316 is defined. Each regressor stage takes as its input the backward prediction errors 313 generated by the multistage lattice prediction filter 312, and the signal to be filtered, denoted d in Haykin FIG. 15.7, but in our case, a respective one of the noise contaminated signals 216 and 218. Each regressor stage separates its noise contaminated input signal into a component $S_{ref}$ which can be built up using linear shifting and weighting of the reference signal, and a component $S_{noref}$ which can not be built up from the reference signal. As a result, from the output of regressor stages 314 and 316, a reconstruction of just the desired pulsatile component of the acquired physiological lead signals is generated as the red and infrared lead signals 30 and 32, respectively.

Saturation Estimate Calculation and Saturation Estimate Post Processing

As previously described in conjunction with FIG. 1, once noise reduced versions of the acquired oximeter signals are developed, they can be processed using conventional ratio processing to develop a blood oxygen saturation estimate. In accordance with the a further aspect of the present invention, the conventional ratio calculation processing is improved. More specifically, as shown in FIG. 3, the above described processing resulted in two sampled oximeter signals, namely 30 and 32, which have been projected into a subspace spanned by a feasible pulse waveform, as defined by the synthetic pulse signal 308. However, in general, the two signals 30 and 32 are not linearly dependent. Therefore, the signals cannot be divided point by point, in accordance with the conventional ratio technique, to obtain a constant saturation estimate.

Thus, in accordance with this further aspect of the invention, a ratio calculator 318 of FIG. 3, projects the thus noise reduced signals 30 and 32 onto a common one-dimensional subspace, τ. Selection of this subspace, τ, can be performed using a minimum disturbance principle which states that the angle between the signal vectors is divided equally. Therefore, the saturation ratio, calculated by $$\omega_{est} = \frac{\langle r_a, \tau \rangle}{\langle r_b, \tau \rangle}$$

reduces to calculating the norm of the red and infrared signals individually over the window of interest (say 201 samples) in NORM processing stage 320, for producing norm signals 322 and 324, respectively. These norm signals are then divided by a RATIO processing stage 326 for generating a sequence of saturation ratio estimates 328. The saturation ratio estimates 328 are converted into blood oxygen saturation estimates for the patient by applying them as addresses to a look up table (LUT) 330, in the conventional manner. This procedure results in a sequence S[n] of saturation estimates 332 being provided by LUT 330.

The final stage of the processing shown in FIG. 3 comprises a filter 334 for processing the sequence of saturation estimates 332 to even further reduce noise and to stabilize the saturation estimates by providing the filtered median of saturation estimates 332 as the final output estimate. In accordance with this aspect of the invention, the sequence of saturation estimates 332 are processed using a two stage filter approach, not specifically shown. In a first filter stage, a median filter is used to remove spikes and outlier values. In a second stage, a nonlinear predictor-corrector filter is used to ensure that the median filter output is integrated and ensures a maximum rate of change.

The median filter maintains a sliding window containing M saturation estimates obtained from earlier stages of the processing, namely, S[n], S[n−1 ] . . . S[n−M+1 ]. Every L seconds, the array is sorted. The top P and bottom P ranked elements are discarded, and the remainder of the data is averaged to obtain a value which is used as a median estimate $\hat{S}_m[n]$ for the next L seconds.

This output of the median filter is subsequently filtered using the following nonlinear predictor-corrector filter:

$$x[n]=(1+60)x[n-1]+\alpha x[n-2]$$

$$x[n]=\hat{x}[n]+\beta \tan h(\hat{S}_m[n]-\hat{x}[n])$$

In our algorithms, we used the following parameters:

| Parameter | Symbol | Value |
| --- | --- | --- |
| Median filter window | M | 1000 samples = 10 s |
| Median filter upper percentile | P | 300 samples = 30% |
| Median filter update frequency | L | 100 samples = 1 s |
| Prediction momentum | α | 0.9 |
| Corrector magnitude | β | 1e-4 |

Thus, what has been shown and described is a novel method and apparatus for reducing noise signals in a physiological signal in a manner which fulfills all the advantages and objects sought therefore. Many changes, modifications, variations and other uses and applications of the subject invention will however be apparent to those of ordinary skill in the art after consideration of this specification and its accompanying drawings, which disclose a preferred embodiment thereof. For example, although in the illustrated embodiment noise is reduced in an oximetry signal, the invention can find applicability for reducing noise in any physiological signal having a pulsatile component. In this regard, although the invention is illustrated in an oximeter, the monitor may in fact comprise a multiparameter monitor that monitors blood oxygen saturation as well as ECG signals. In this case, the ECG signals themselves can be used to determine an estimate of the heart rate value, or alternatively, the heart rate value can be determined by means other than by use of an ECG signal, and for example, by use of an ultrasound, accelerometer, nuclear magnetic resonance, electrical impedance, or other signal acquiring technique.

Furthermore, in the illustrated embodiment the synthetic reference signal is generated so as to be piecewise constant in frequency, and the shape of the synthetic kernel is invariant and fixed beforehand. In an alternative embodiment, straightforward modifications can be made where the kernel function is segmented from the high-confidence sections of the lead signal.

Additionally, when using the adaptive filter technique described in the preferred embodiment, alternative techniques can be used to measure the noise levels in the acquired physiological signals, and the sensitivity or weighting given to the saturation and signal estimates in the various signal sections can be adjusted based on the noise estimates. Examples of such noise estimates are the existing error codes 228, the fraction of the signal power filtered out by the adaptive filter, or the width of the FFT spectral peak.

Means could be provided to develop more reasonable initialization settings. That is, the adaptive filter and outlier detector performance could be sub-optimal during the first 20 to 30 seconds of operation, since not enough data is available in such a short time to get good estimates of the signal statistics. An existing heart rate estimator which can produce a heart rate estimate in a shorter period of time can be used for reference generation.

Finally, the statistics generated by the outlier detection system can be used to further filter the incoming lead signals, for example, by clipping excessively large sample values at some secondary threshold value before inputting these signals to the adaptive filter.

In view of the above, the scope of the invention is intended to be limited only by the following claims.

What I claim is:

1. A method for reducing the level of an undesired noise component in an acquired signal having a desired signal component, comprising the following steps:

acquiring a signal;

generating a synthetic reference signal that is modeled to exhibit a correlation with the desired signal component of the acquired signal;

applying to one input of an adaptive filter arrangement said acquired signal, and to another input of said adaptive filter arrangement said synthetic reference signal; and operating said adaptive filter arrangement in a feedback manner, so that the adaptive filter arrangement iteratively adjusts the applied synthetic reference signal so as to progressively generate as an output of the filter arrangement a more accurate approximation of the desired signal component of the acquired signal.

2. The method of claim 1, wherein said generating step comprises:

generating said reference signal by processing a predetermined kernel function that is representative of a pulsatile cycle of the desired signal component of the acquired signal.

3. The method of claim 1, wherein the operating step of said adaptive filter comprises:

shifting and weighting of said synthetic reference signal using a multistage lattice prediction filter to generate backward prediction error signals; and combining said acquired signal with shifted and weighted version of said backward prediction error signals, to iteratively build-up a reconstruction of the desired component of said acquired signal.

4. The method of claim 1, including a further step of:

confidence processing of the acquired signal so as to identify sections thereof having a high confidence of being relatively noise-free.

5. The method of claim 4, wherein said acquiring step acquires a physiological signal from a patient.

6. The method of claim 5, including a further step of:

processing of said high confidence sections of the acquired physiological signal to develop values that are used to adjust the generation of the synthetic reference signal so that it exhibits a greater correlation with the desired signal component of the acquired physiological signal.

7. The method of claim 6, wherein:

said acquiring step comprises acquiring first and second ones of acquired physiological signals; and said confidence processing step comprises subjecting the first and second ones of said acquired physiological signals to a correlation test, and then identifying sections of each of said acquired physiological signals that exhibit a correlation that exceeds a predetermined threshold level as being relatively noise-free, and identifying sections of each of said acquired physiological signals that exhibit a correlation that does not exceed the predetermined threshold level as being relatively noisy.

8. The method of claim 6, wherein said processing of said high confidence sections of said acquired physiological comprises FFT processing of said high confidence sections to develop a value representative of at least a fundamental frequency component of the desired signal component of the acquired physiological signal, which value is used to adjust the modeling of the synthetic reference signal so as to increase its correlation with the desired signal component of the acquired physiological signal.

9. The method of claim 6, wherein said confidence processing comprises:

subjecting said acquired physiological signal to an amplitude threshold test; and identifying sections of said acquired physiological signal that have an amplitude that does not exceed a predetermined amplitude threshold level as being relatively noise-free, and identifying sections of said acquired physiological signal that have an amplitude that does exceed the predetermined amplitude threshold level as being relatively noisy.

10. The method of claim 9, wherein:

said acquiring step comprises acquiring first and second ones of acquired physiological signals; and said confidence processing step comprises subjecting the first and second ones of said acquired physiological signals to a correlation test, and then identifying sections of each of said acquired physiological signals that exhibit a correlation that exceeds a predetermined threshold level as being relatively noise-free, and identifying sections of each of said acquired physiological signals that exhibit a correlation that does not exceed the predetermined threshold level as being relatively noisy.

11. The method of claim 10, wherein said confidence processing step comprises the further steps of:

developing an error code stream comprising a sequence of error codes that identify corresponding successive sections of said acquired physiological signals that have been identified as being either relatively noise-free or noisy; and morphological processing of said error code stream to increase the degree of confidence that sections of said acquired physiological signal identified as being relatively noise-free or relatively noisy have been correctly identified.

12. The method of claim 11, wherein said morphological processing step comprises:

erosion of said error code stream, by changing a sequence of contiguous error codes in said error code stream to identify as noisy those of said error codes previously identified as relatively noise-free but having a sequence length that is less than a first predetermined length M, and dilation of said error code stream, by changing a sequence of contiguous error codes in said error code stream to identify as relatively noise-free those of said error codes previously identified as noisy but having a sequence length that is less than a second predetermined length L.

13. The method of claim 12, wherein said erosion step sets said length M to be greater than said length L.

14. Apparatus for reducing the level of an undesired noise component in an acquired physiological signal having a desired signal component, comprising:

a sensor arrangement for acquiring a physiological signal;

a signal generator for modeling a synthetic reference signal that exhibits a correlation with the desired signal component of the acquired physiological signal; and an adaptive filter arrangement having a first input responsive to said acquired physiological signal, and a second input responsive to said synthetic reference signal, said adaptive filter arrangement being operated in a feedback manner so as to iteratively adjust the modeled synthetic reference signal and progressively generate as an output of the filter arrangement a more accurate approximation of the desired signal component.

15. The apparatus of claim 14, wherein said signal generator comprises:

a processor that is responsive to a predetermined kernel function representative of a pulsatile cycle of the desired signal component of the acquired physiological signal.

16. The apparatus of claim 14, wherein said adaptive filter comprises:

a multistage lattice prediction filter for shifting and weighting of said synthetic reference signal to generate backward prediction error signals; and a regressor processing stage for iteratively combining said acquired physiological signal with shifted and weighted versions of said backward prediction error signals, to progressively build-up a reconstruction of the desired component of said acquired physiological signal.

17. The apparatus of claim 14, including:

a confidence processor for processing the acquired physiological signal so as to identify sections thereof having a high confidence of being relatively noise-free.

18. The apparatus of claim 17, further including:

an extraction processor responsive to the acquired physiological signal and to the confidence processor, so as to only process said high confidence sections of the acquired physiological signal, and in response to said processing develop a value that is used to adjust the generation of the synthetic reference signal so that it exhibits a greater correlation with the desired signal component of the acquired physiological signal.

19. The apparatus of claim 18, wherein:

said sensor arrangement acquires first and second ones of acquired physiological signals; and said confidence processor comprises:

a correlation detector for subjecting the first and second ones of said acquired physiological signals to a correlation test; and an error code tagger responsive to said correlation detector for identifying sections of each of said acquired physiological signals that exhibit a correlation that exceeds a predetermined threshold level as being relatively noise-free, and identifying sections of each of said acquired physiological signals that exhibit a correlation that does not exceed the predetermined threshold level as being relatively noisy.

20. The apparatus of claim 18, wherein said extraction processor comprises:

an FFT processor responsive to said confidence processor, for processing only those sections of the first and second ones of said acquired physiological signals that are identified to have a high confidence of being relatively noise-free, to develop a value representative of at least a fundamental frequency component of the desired signal component of the acquired physiological signal, which value is used to adjust the modeling of the synthetic reference signal so as to increase its correlation with the desired signal component of the acquired physiological signal.

21. The apparatus of claim 18, wherein said confidence processor comprises:

an amplitude detector for subjecting said acquired physiological signal to an amplitude threshold test; and an error code tagger for identifying sections of said acquired physiological signal that have an amplitude that does not exceed a predetermined amplitude threshold level as being relatively noise-free, and identifying sections of said acquired physiological signal that have an amplitude that does exceed the predetermined amplitude threshold level as being relatively noisy.

22. The apparatus of claim 21, wherein:

said sensor arrangement acquires first and second ones of acquired physiological signals; and said confidence processor includes:

a correlation detector for subjecting the first and second ones of said acquired physiological signals to a correlation test; and said error code tagger is responsive to said correlation detector for developing an error code stream that identifies sections of each of said acquired physiological signals that exhibit a correlation that exceeds a predetermined threshold level as being relatively noise-free, and identifies sections of each of said acquired physiological signals that exhibit a correlation that does not exceed the predetermined threshold level as being relatively noisy.

23. The apparatus of claim 22, wherein said extraction processor comprises:

an FFT processor responsive to said error code stream and the first and second ones of said acquired physiological signals, for processing only those sections of the first and second ones of said acquired physiological signals that are identified by said error code stream to have a high confidence of being relatively noise-free, to develop a value representative of at least a fundamental frequency component of the desired signal component of the acquired physiological signals, which value is used to adjust the modeling of the synthetic reference signal so as to increase its correlation with the desired signal component of the acquired physiological signals.

24. The apparatus of claim 22, further including.

a morphological processor for processing the error code stream to increase the degree of confidence that sections of said acquired physiological signal identified as being relatively noise-free or relatively noisy have been correctly identified.

25. The apparatus of claim 24, wherein said morphological processor comprises:

an eroder for eroding said error code stream, by changing a sequence of contiguous error codes in said error code stream to identify as noisy those of said error codes previously identified as relatively noise-free but having a sequence length that is less than a first predetermined length M, and a dilator for dilating said error code stream, by changing a sequence of contiguous error codes in said error code stream to identify as relatively noise-free those of said error codes previously identified as noisy but having a sequence length that is less than a second predetermined length L.

* * * * *